United States Patent [19]
Fischer et al.

[11] Patent Number: 5,952,533
[45] Date of Patent: Sep. 14, 1999

[54] METHOD OF PRODUCING 1,6-HEXANE DIOL FROM EPOXYBUTADIENE

[75] Inventors: Rolf Fischer; Detlef Kratz, both of Heidelberg; Rolf Pinkos, Bad Dürkheim; Martin Schäfer, Ludwigshafen; Arthur Höhn, Kirchheim, all of Germany

[73] Assignee: BASF Aktiengesellschaft, Ludwigshafen, Germany

[21] Appl. No.: 09/077,599

[22] PCT Filed: Dec. 11, 1996

[86] PCT No.: PCT/EP96/05524

§ 371 Date: Jun. 2, 1998

§ 102(e) Date: Jun. 2, 1998

[87] PCT Pub. No.: WO97/22601

PCT Pub. Date: Jun. 26, 1997

[30] Foreign Application Priority Data

Dec. 18, 1995 [DE] Germany .......................... 195 47 213

[51] Int. Cl.⁶ .................................................. C07C 27/00
[52] U.S. Cl. .............................................. 568/865; 549/513
[58] Field of Search ................................................ 568/865

[56] References Cited

U.S. PATENT DOCUMENTS 2,561,984  7/1951  Hillyer .
3,070,633  12/1962  Utne .
5,395,992  3/1995  Ricci ........................................ 568/865

FOREIGN PATENT DOCUMENTS

97/22601  5/1997  WIPO .

OTHER PUBLICATIONS

Industrielle Organische Chemie, 1994, 263, Weissermel.
Carbohydrate Res. vol. 82 (1980). 73–72, Kuszmann.

*Primary Examiner*—Michael L. Shippen
*Attorney, Agent, or Firm*—Keil & Weinkauf

[57] ABSTRACT

1,6-Hexanediol is prepared by
a) Reacting epoxybutadiene in the presence of a metathesis catalyst with elimination of ethene to give bisepoxyhexatrienes of the formulae Ia and Ib

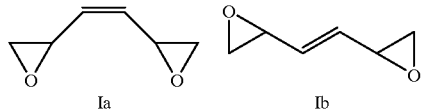

and
b) hydrogenating these bisepoxyhexatrienes with hydrogen to give 1,6-hexanediol.

8 Claims, No Drawings

METHOD OF PRODUCING 1,6-HEXANE DIOL FROM EPOXYBUTADIENE

The present invention relates to a novel process for preparing 1,6-hexanediol from epoxybutadiene.

1,6-Hexanediol is an important intermediate in the preparation of polyesters and polyurethanes. U.S. Pat. No. 3,070,633 describes a process for preparing 1,6-hexanediol by hydrogenation of 2,5-tetrahydrofurandimethanol. It is prepared on an industrial scale by hydrogenation of adipic acid or its derivatives (Weissermel, Arpe, Industrielle Organische Chemie, 4th edition, Verlag Chemie 1994, p. 263). A disadvantage of these processes is the use of corrosive streams which require expensive materials of construction. Furthermore, the hydrogenation is only economical at high pressures, so that suitable reactors incur high capital costs. Finally, the hydrogenation of one equivalent of adipic acid requires 4 equivalents of hydrogen.

The preparation of bisepoxyhexatrienes of the formulae Ia und Ib

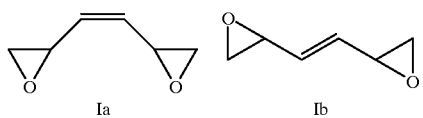

is possible, according to Kuszmann et al., Carbohydrate Research, 83 (1980) 63, by reacting ditosylates or dimesylates of tetrols with superstoichiometric amounts of base. Since, however, the precursors required are complicated to prepare and the method is linked to the formation of stoichiometric amounts of salt, it is not suitable for the preparation of the bisepoxytrienes in large amounts.

It is an object of the present invention to provide a process which allows the preparation of 1,6-hexanediol at significantly lower pressures than are used in the prior art. Furthermore, the process should be able to be carried out using less hydrogen per equivalent of hexanediol. A further aspect of the object of the present invention is to find a process which makes possible the preparation of bisepoxyhexatrienes of the formulae Ia and Ib while avoiding the abovementioned disadvantages of the prior art.

We have found that this object is achieved by a process for preparing 1,6-hexanediol, which comprises
a) Reacting epoxybutadiene in the presence of a metathesis catalyst with elimination of ethene to give bisepoxyhexatrienes of the formulae Ia and Ib and
b) hydrogenating these bisepoxyhexatrienes with hydrogen to give 1,6-hexanediol.

The overall process for preparing 1,6-hexanediol from epoxybutadiene is shown in the following reaction equation:

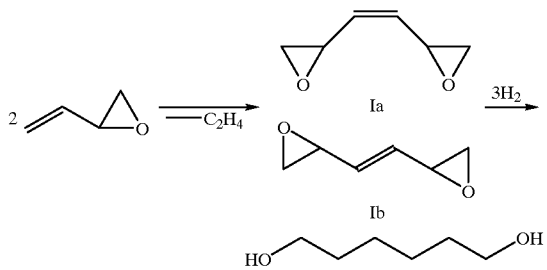

Process step a)

According to the present invention, 2 equivalents of epoxybutadiene are reacted with elimination of ethene to give the bisepoxytrienes of the formulae Ia and Ib. According to U.S. Pat. No. 4,897,498, epoxybutadiene can be prepared by epoxidation of butadiene. It is preferably used in pure form, but can also contain secondary constituents such as crotonaldehyde, 2,3-dihydrofuran and 2,5-dihydrofuran. The reaction takes place in the presence of a metathesis catalyst. These are catalysts which establish an equilibrium of the type

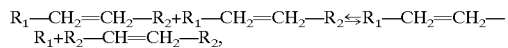

where $R_1$ and $R_2$ are organic radicals. The catalysts are known per se, and are heterogeneous or homogeneous transition metal compounds, in particular those of transition metals of groups 4 and 6–10 of the Periodic Table of the Elements. Such catalysts are described, for example, in Parshall, Ittel, Homogeneous Catalysis, 2nd edition, Wiley 1992, pp. 217–236, also in Banks, Catalysis, Vol. 4, pp. 100–129 and in Grubbs, Progress in Inorg. Chem., Vol. 24, pp. 1–50.

Preferred metathesis catalysts contain ruthenium. Particularly preferred catalysts are ruthenium compounds of the general composition $RuX_2(=CHR)(PR'_3)_2$, where X is a halogen such as fluoro, chloro, bromo and iodo, R is hydrogen, alkyl cycloalkyl, aryl or aralkyl and R' is alkyl, cycloalkyl, aryl or aralkyl, as are described in WO-A 93/20111. Particular preference is also given to catalysts of the composition $RuX_2(Arene)/PR_3$, where X is a halogen such as fluorine, chlorine, bromine and iodine and R is hydrogen, alkyl, cycloalkyl, aryl or aralkyl, as are described, also in combination with a diazoalkane compound, in Noels, J. Chem. Soc., Chem. Commun. 1995, pp. 1127–1128. Examples which may be mentioned are $RuCl_2$ (=CHPh) $(PCy_3)_2$, $RuCl_2(p\text{-cumene})/PCy_3/N_2CHSiMe_3$ and $RuCl_2(p\text{-cumene})$ $(PCy_3)$, where Ph is phenyl and Cy is cyclohexyl.

The amount of the catalyst, based on epoxybutadiene, can be varied within wide limits, e.g. from $10^{-5}$ to 1 mol/mol of epoxybutadiene, preferably from $10^{-4}$ to $10^{-1}$ mol, particularly preferably from $2\times10^{-4}$ to $5\times10^{-2}$ mol/mol of epoxybutadiene.

The reaction of epoxybutadiene over said catalysts can be carried out in the gas or liquid phase. The metathesis is generally carried out at from $-20$ to $400°$ C. Preference is given to carrying out the reaction in the liquid phase at from $-10$ to $150°$ C., particularly preferably from 15 to $100°$ C. The pressure is advantageously selected such that at least epoxybutadiene is present in liquid form.

The reaction can be carried out continuously or batchwise.

The ethene liberated during the reaction is preferably removed continuously from the reaction mixture. Ethene can be driven out using an inert gas such as methane, nitrogen, argon or carbon dioxide. However, preference is given to a process procedure in which ethene leaves the reactor as a result of the intrinsic vapor pressure established.

The metathesis stage can be carried out in the presence or absence of a solvent. Examples of suitable solvents are: ethers such as tetrahydrofuran, ethylene glycol dimethyl ether, diethyl ether and methyl tert-butyl ether, hydrocarbons such as cyclohexane, benzene, toluene and cumene, halogenated hydrocarbons such a chloroform, methylene chloride, dichloroethanes, chloropropanes and chlorobutanes and also esters such as ethyl acetate.

Suitable reactors for the metathesis reaction are, for example, stirred vessels, loop reactors or tube reactors. It has been found to be advantageous to carry out small batches in particular under a protective gas atmosphere, for example under argon.

The metathesis is generally complete after a reaction time of from 0.5 to 48 hours. The reaction mixture obtained can be subjected directly to hydrogenation. If, however, the bisepoxyhexatrienes obtained according to the present invention are to be isolated, all volatile constituents of the reaction mixture can be separated by distillation from the catalyst. The catalyst remains in the distillation bottoms and can, if appropriate after work-up, be returned to the reaction. The bisepoxyhexatrienes of the formulae Ia and Ib can be separated by distillation from the starting compound which can likewise be returned to the reaction.

Process step b)

The compounds of the formulae Ia and Ib obtained as described in process step a) can be converted into 1,6-hexanediol by hydrogenation. For this purpose, the reaction mixture from the metathesis can, if the metathesis catalyst is present therein in homogeneous form, be hydrogenated directly with hydrogen without addition of a further hydrogenation catalyst. Should complete conversion not have been achieved in the metathesis stage, it is advantageous to separate off the epoxybutadiene by distillation prior to the hydrogenation. If this separation is omitted, n-butanol can generally be obtained from epoxybutadiene under the hydrogenation conditions for preparing 1,6-hexanediol.

In a preferred embodiment, the metathesis catalyst is separated from the reaction mixture after the metathesis reaction is complete and is recycled, and the bisepoxyhexatrienes are hydrogenated. The hydrogenation is carried out over a hydrogenation catalyst known per se. Suitable catalysts for the process stage b) are those which make possible the hydrogenation of olefins, ketones or aldehydes with hydrogen to give hydrocarbons or alcohols. These catalysts, as are described, for example, in Kropf, Methoden der Organischen Chemie, Houben-Weyl, Thieme Verlag 1980, vol. IV/1c, pp. 45–66, can be present in the reaction mixture in homogeneous form.

However, preferred hydrogenation catalysts are heterogeneous catalysts as are described, for example, in Kropf, Methoden der Organischen Chemie, Houben-Weyl, Thieme Verlag 1980, vol. IV/1c, p. 16–44. The hydrogenation catalysts thus comprise, for example, elements of groups 6 to 11 of the Periodic Table of the Elements. These can be present in the form of metals, oxides or sulphides. They can be used, for example, as supported catalysts, skeletal catalysts, metal blacks or as metallic mixed catalysts. Examples are Pt black, Pt/C, Pt/Al$_2$O$_3$, PtO$_2$, Pd black, Pd/C, Pd/Al$_2$O$_3$, Pd/SiO$_2$, Pd/CaCO$_3$, Pd/BaSO$_4$, Rh/C, Rh/Al$_2$O$_3$, Ru/SiO$_2$, Ni/SiO$_2$, Raney nickel, Co/SiO$_2$, Co/Al$_2$O$_3$, Raney cobalt, Fe, Fe-containing mixed catalysts, Re black, Raney rhenium, Cu/SiO$_2$, Cu/Al$_2$O$_3$, Raney copper, Cu/C, PtO$_2$/Rh$_2$O$_3$, Pt/Pd/C, CuCr$_2$O$_4$, BaCr$_2$O$_4$, Ni/Cr$_2$O$_3$/Al$_2$O$_3$, Re$_2$O$_7$, CoS, NiS, MOS$_3$, Cu/SiO$_2$/MoO$_3$/Al$_2$O$_3$. Particular preference is given to catalysts comprising elements of groups 7 to 10 of the Periodic Table of the Elements for example Pd/C, Pt/C, Re/C, Cu/C, Cu/SiO$_2$, Ni/C, Raney nickel and Raney cobalt. Prior to use, the catalysts can be activated in a manner known per se by heating in a hydrogen atmosphere.

The hydrogenation can be carried out continuously or batchwise. The hydrogen pressure can be from 1 to 300 bar, preferably from 1 to 100 bar, particularly preferably from 1 to 50 bar, at a reaction temperature of from 20 to 300° C., preferably from 20 to 200° C. and particularly preferably from 20 to 150° C.

The hydrogenation of the bisepoxyhexatrienes can be carried out in bulk or in a solvent. Examples of suitable solvents are ethers such as ethylene glycol dimethyl ether, tetrahydrofuran, dioxane and diethyl ether, alcohols such as methanol, ethanol, propanol and 1,6-hexanediol, and also water.

The 1,6-hexanediol prepared according to the present invention can be isolated from the reaction mixture in a manner known per se, for example by distillation.

The process of the present invention for preparing 1,6-hexanediol from epoxybutadiene results, if the preparation of the respective starting compounds is also taken into account, in fewer process stages to the desired end product than the known processes using adipic acid or their derivatives. Furthermore, the hydrogenation stage can be configured as a low-pressure or intermediate-pressure process which, compared with the prior art, is substantially simpler in terms of process technology and also incurs significantly lower capital costs. Finally, in the hydrogenation stage, only 3 equivalents of hydrogen are required per equivalent of 1,6-hexanediol.

EXAMPLES

The epoxybutadiene used in the examples had a purity of about 99%.

Process stage a)

Example 1

20 mg of Cl$_2$(PCy$_3$)$_2$Ru=C(Ph)H (Cy=cyclohexyl, Ph=phenyl) and 3 g of epoxybutadiene were stirred under argon protective gas for 21 hours at 24° C., with the ethene liberated being able to escape. Analysis of the reaction mixture by gas chromatography indicated a conversion of 3.1% to the compounds Ia and Ib at a selectivity of 12%.

Example 2

10 mg of RuCl$_2$(p-cumene)PCy$_3$ (Cy=cyclohexyl) and 2 g of epoxybutadiene were, similarly to Example 1, stirred for 23 hours at 23° C. The process products Ia and Ib were obtained in a selectivity of 15% at a conversion of 3.5%.

Example 3

10 mg of RuCl$_2$(p-cumene)PCy$_3$ were admixed with 50 mg of trimethylsilyldiazomethane, heated at 60° C. for 2 minutes, cooled to 23° C. and admixed with 2 g of epoxybutadiene. After a reaction carried out similarly to Example 1, the process products Ia and Ib were obtained after 19.5 hours in a selectivity of 15% at a conversion of 2.6%.

Process stages a) and b)

Example 4

Using a method similar to Example 1, 20 mg of Cl$_2$(PCy$_3$)$_2$Ru=C(Ph)H and 6 g of epoxybutadiene were reacted. After the metathesis reaction was complete, unreacted epoxybutadiene was distilled off and the residue of 0.11 g was admixed with 5 g of tetrahydrofuran and 1.2 g of Raney cobalt. The mixture was hydrogenated for 2 hours at 120° C. and a hydrogen pressure of 40 bar, with the bisepoxyhexatrienes present in the mixture being converted completely into 1,6-hexanediol.

Example 5

Using a method similar to Example 1, 80 mg of Cl$_2$(PCy$_3$)$_2$Ru=C(Ph)H and 11.9 g of epoxybutadiene were reacted. The process products Ia and Ib were obtained in a selectivity of 24% at a conversion of 3.2%. Unreacted epoxybutadiene was separated by distillation from the reaction mixture and the residue was taken up in 6 g of ethylene glycol dimethyl ether. This solution was hydrogenated for 1 hour at 100° C. and a hydrogen pressure of 50 bar, with the bisepoxyhexatrienes present in the mixture being converted completely into 1,6-hexanediol.

We claim:

1. A process for preparing 1,6-hexanediol, which comprises
   a) reacting epoxybutadiene in the presence of a metathesis catalyst with elimination of ethene to give bisepoxyhexatrienes of the formulae Ia and Ib

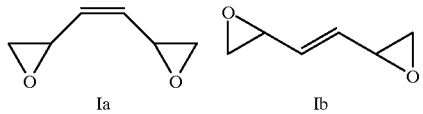

and b) hydrogenating these bisepoxyhexatrienes with hydrogen to give 1,6-hexanediol.

2. A process as defined in claim 1, wherein ruthenium compounds are used as metathesis catalyst.

3. A process as defined in claim 1, wherein the ethene liberated during the reaction according to process step a) is removed continuously.

4. A process as defined in claim 1, wherein the process step a) is carried out at from 15 to 100° C.

5. A process as defined in claim 1, wherein the process step a) is carried out at a pressure at which the epoxybutadiene is present in liquid form.

6. A process as defined in claim 1, wherein the hydrogenation according to process step b) is carried out in the presence of the metathesis catalyst.

7. A process as defined in claim 1, wherein the hydrogenation according to process step b) is carried out after the separation of the metathesis catalyst in the presence of a hydrogenation catalyst.

8. A process as defined in claim 1, wherein bisepoxyhexatrienes of the formulae Ia and Ib

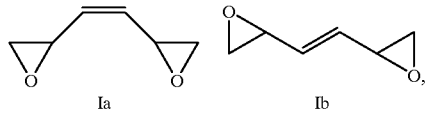

are prepared by reacting epoxybutadiene in the presence of a metathesis catalyst with elimination of ethene.

* * * * *